United States Patent
Broyer et al.

(10) Patent No.: US 11,999,936 B2
(45) Date of Patent: Jun. 4, 2024

(54) EXTRACTION SYSTEM AND METHOD FOR EXTRACTING MICROORGANISMS CONTAINED IN A SAMPLE

(71) Applicant: BIOMÉRIEUX, Marcy-l'Etoile (FR)

(72) Inventors: Patrick Broyer, Saint Cassien (FR);
Marie-Hélène Charles, Condrieu (FR);
Jérôme Blaze, La Terrasse (FR);
Nadine Perrot, Montluel (FR);
Frédéric Pinston, Grenoble (FR);
Hervé Rostaing, Le Versoud (FR)

(73) Assignee: BIOMÉRIEUX, Marcy l'Etoile (FR)

( * ) Notice: Subject to any disclaimer, the term of this patent is extended or adjusted under 35 U.S.C. 154(b) by 510 days.

(21) Appl. No.: 16/461,007

(22) PCT Filed: Nov. 15, 2017

(86) PCT No.: PCT/FR2017/053121
§ 371 (c)(1),
(2) Date: May 15, 2019

(87) PCT Pub. No.: WO2018/091818
PCT Pub. Date: May 24, 2018

(65) Prior Publication Data
US 2019/0270958 A1  Sep. 5, 2019

(30) Foreign Application Priority Data
Nov. 15, 2016  (FR) ...................................... 16/61015

(51) Int. Cl.
*C12M 3/00* (2006.01)
*B01L 3/00* (2006.01)
(Continued)

(52) U.S. Cl.
CPC ............. *C12M 33/14* (2013.01); *B01L 3/502* (2013.01); *C12M 23/12* (2013.01); *C12M 23/16* (2013.01);
(Continued)

(58) Field of Classification Search
CPC .............................. C12M 33/14; C12M 23/12
See application file for complete search history.

(56) References Cited

U.S. PATENT DOCUMENTS 5,945,070 A * 8/1999 Kath .................... B01J 19/0046
422/537
9,259,734 B2 * 2/2016 Williams .............. F16K 99/003
(Continued)

FOREIGN PATENT DOCUMENTS

EP        2 453 219 A1    5/2012
WO    2013/016211 A1    1/2013
(Continued)

OTHER PUBLICATIONS

Feb. 23, 2018 Written Opinion issued in International Patent Application No. PCT/FR2017/053121.
(Continued)

*Primary Examiner* — Nathan A Bowers
(74) *Attorney, Agent, or Firm* — Oliff PLC (57) ABSTRACT

An extraction system includes a support bar including a sample well, a reagent well, at least one washing well, and at least one protection and retention housing; a pipetting element removably mounted on the support bar and extending at least partially into the at least one protection and retention housing; and a filtering and transfer device configured to capture and accumulate microorganisms contained in the sample and transfer the captured and accumulated microorganisms, the filtering and transfer device being removably mounted on the support bar and extending at
(Continued)

least partially into the at least one protection and retention housing. The filtering and transfer device includes a hollow body having an elongated shape and including a proximal end portion and a distal end portion; and a filtering element fixed to the distal end portion of the hollow body.

17 Claims, 5 Drawing Sheets

(51) Int. Cl.

| | | |
|---|---|---|
| *C12M 1/26* | (2006.01) | |
| *C12M 1/32* | (2006.01) | |
| *C12M 3/06* | (2006.01) | |
| *G01N 33/00* | (2006.01) | |
| *G01N 33/68* | (2006.01) | |
| *G16B 20/00* | (2019.01) | |
| *B01L 9/06* | (2006.01) | |
| *G01N 1/40* | (2006.01) | |
| *G01N 35/04* | (2006.01) | |

(52) U.S. Cl.
CPC ......... *G01N 33/6848* (2013.01); *G16B 20/00* (2019.02); *B01L 9/06* (2013.01); *G01N 1/4005* (2013.01); *G01N 2035/0436* (2013.01)

(56) References Cited

U.S. PATENT DOCUMENTS

| | | | | |
|---|---|---|---|---|
| 11,598,784 | B2 * | 3/2023 | Tan | G01N 33/54366 |
| 2002/0164779 | A1 * | 11/2002 | Cocola | B01L 3/50855 |
| | | | | 435/287.2 |
| 2003/0099576 | A1 * | 5/2003 | Li | B01L 3/0275 |
| | | | | 422/400 |
| 2004/0161368 | A1 * | 8/2004 | Holtlund | G01N 35/10 |
| | | | | 422/68.1 |
| 2005/0181513 | A1 * | 8/2005 | Lopez-Avila | H01J 49/0418 |
| | | | | 250/288 |
| 2006/0120926 | A1 * | 6/2006 | Takada | B01L 3/50853 |
| | | | | 422/400 |
| 2009/0129978 | A1 * | 5/2009 | Wilson | C08G 83/003 |
| | | | | 422/400 |
| 2011/0008825 | A1 * | 1/2011 | Ingber | G01N 21/0303 |
| | | | | 435/288.1 |
| 2011/0020921 | A1 * | 1/2011 | Kluttz | B01L 7/525 |
| | | | | 435/287.2 |
| 2012/0115238 | A1 * | 5/2012 | Akashi | B01L 3/502 |
| | | | | 436/94 |
| 2012/0156716 | A1 * | 6/2012 | Walsh | B01L 3/561 |
| | | | | 422/534 |
| 2013/0045532 | A1 * | 2/2013 | Hyman | C12N 1/06 |
| | | | | 435/306.1 |
| 2014/0302611 | A1 * | 10/2014 | Orning | B01L 3/50 |
| | | | | 436/71 |
| 2014/0377785 | A1 * | 12/2014 | Janetzko | G01N 33/54386 |
| | | | | 435/7.92 |

FOREIGN PATENT DOCUMENTS

| | | |
|---|---|---|
| WO | 2013/068760 A2 | 5/2013 |
| WO | 2015/054113 A1 | 4/2015 |

OTHER PUBLICATIONS

Feb. 23, 2018 International Search Report issued in International Patent Application No. PCT/FR2017/053121.

* cited by examiner

EXTRACTION SYSTEM AND METHOD FOR EXTRACTING MICROORGANISMS CONTAINED IN A SAMPLE

The present invention relates to an extraction system and method for extracting microorganisms contained in a sample, with the aim notably of identifying and/or characterizing the microorganisms extracted for example by a MALDI-TOF MS mass spectrometry analysis on an analysis plate, or an antibiogram analysis.

A first known method for extracting microorganisms contained in a positive sample, such as a positive blood culture, consists of:
- manually depositing several drops of the sample on one or more culture media in Petri dishes,
- incubating the Petri dish or dishes for 18 to 48 hours depending on the type of microorganisms,
- manually withdrawing a portion of the colonies on the Petri dishes,
- manually depositing the colonies withdrawn on different places of a MALDI-TOF MS analysis plate, also called MALDI-TOF MS mass spectrometry analysis plate,
- performing mass spectrometry identification on the MALDI-TOF MS analysis plate.

A second known method for extracting microorganisms contained in a positive sample, such as a positive blood culture, consists of:
- manually depositing several drops of the sample on one or more culture media in Petri dishes,
- incubating the Petri dish or dishes for 18 to 24 hours,
- manually withdrawing a portion of the colonies on the Petri dishes,
- preparing a concentrated suspension of microorganisms, calibrated for optical density, from the colonies withdrawn,
- performing an antibiogram analysis on the suspension withdrawn.

These first and second known extraction methods are long and notably require the presence of an experienced operator for performing the large number of manual steps.

Automatic machines have thus been developed for performing notably the withdrawing and depositing steps employed for the methods described above.

However, these automatic machines require a very substantial financial investment for an analytical laboratory but without appreciably reducing the duration of these extraction methods.

Document WO2013/016211 describes a method for extracting microorganisms contained in a positive sample, notably comprising the use of a filtering and transfer device for isolating the microorganisms contained in the positive sample and for transferring them notably onto a MALDI-TOF MS analysis plate.

Such a method can greatly reduce the duration of extraction of microorganisms contained in a positive sample. However, such an extraction method still requires the prolonged presence of an experienced operator for performing the various manual steps throughout the process. Moreover, depositing on a MALDI-TOF MS analysis plate is not standardized in terms of deposition, and cannot easily ensure traceability of the results.

The present invention aims to remedy these drawbacks.

The technical problem on which the invention is based therefore consists of supplying an extraction system which is of simple and compact construction, while allowing rapid, automated extraction of microorganisms contained in a positive sample for analysis on a MALDI-TOF MS analysis plate or for an antibiogram from a concentrated suspension of microorganisms.

For this purpose, the present invention relates to an extraction system for extracting microorganisms contained in a sample, said extraction system comprising:
- a support bar comprising:
  - a sample well configured to receive a sample containing microorganisms, such as a positive blood culture,
  - a reagent well configured to contain a selective lysis buffer,
  - at least one washing well configured to contain a washing reagent, and
  - at least one protection and retention housing,
- a pipetting element removably mounted on the support bar and extending at least partially into the at least one protection and retention housing,
- a filtering and transfer device configured to capture and accumulate microorganisms contained in the sample and transfer the captured and accumulated microorganisms, the filtering and transfer device being removably mounted on the support bar and extending at least partially into the at least one protection and retention housing, said filtering and transfer device comprising:
  - a hollow body having an elongated shape and comprising a proximal end portion and a distal end portion, and
  - a filtering element fixed to the distal end portion of the hollow body.

This configuration of the extraction system ensures that it is very compact, and moreover allows it to be loaded easily, via a rack, in an automatic machine notably able to manipulate the pipetting element and the filtering and transfer device for automatically performing the various steps of extraction of the microorganisms contained in a positive sample placed in the sample well.

Furthermore, use of the extraction system according to the present invention does not require special training or skill. In fact, the only manual steps that have to be carried out by an operator are placing the sample in the sample well, positioning the support bar on a rack and loading the rack in the automatic machine. Moreover, the simplicity of using the extraction system according to the present invention makes it possible to treat urgent blood cultures in night-time service, with a greatly reduced technical level.

Moreover, in conjunction with the automatic machine, the extraction system according to the present invention means it is not necessary to immobilize a technician throughout all of the manual operations for extraction, making it possible to deliver a MALDI-TOF MS analysis plate with deposits that are reproducible and standardized in terms of the amount deposited and are directly usable in the MALDI-TOF MS analysis system for identifying or characterizing the pathogens present in the sample.

Finally, the use of a filtering and transfer device similar to that described in document WO2013/016211 ensures rapid extraction of the microorganisms contained in a sample loaded in the sample well, and reliable deposition of the microorganisms on a MALDI-TOF MS analysis plate.

As a result, the extraction system according to the present invention allows rapid, automated extraction of the microorganisms contained in a positive sample for analysis on a MALDI-TOF MS analysis plate or for an antibiogram.

It should, moreover, be noted that the configuration of the extraction system allows considerable reduction of the costs of manufacture of the automatic machine that is able to perform automatic extraction of the microorganisms, notably because the various reagents required are already present on each support bar and therefore do not have to be stored in the automatic machine.

The extraction system may, moreover, have one or more of the following features, taken alone or in combination.

According to one embodiment of the invention, the sample well, the reagent well and the at least one washing well are approximately aligned in the direction of extension of the support bar.

According to one embodiment of the invention, the distal end portion of the hollow body and the filtering element extend into the at least one protection and retention housing.

According to one embodiment of the invention, the pipetting element comprises a distal end portion extending at least partially into the at least one protection and retention housing.

According to one embodiment of the invention, the at least one protection and retention housing is configured for retaining drops of liquid, such as drops of sample or of reagents, that are able to flow by gravity from the pipetting element and the filtering and transfer device.

According to one embodiment of the invention, the filtering element is configured for retaining at least one portion of the microorganisms contained in the sample and for allowing other elements contained in the sample to pass through, such as elements that are not micro-organic, for example cellular debris, or lysed blood components, such as erythrocytes.

According to one embodiment of the invention, the filtering element is a filtration membrane, such as a membrane of the Pall SuporR type (PES material), for example in the form of a disk or dome.

According to one embodiment of the invention, the filtering element consists of a material selected from the group notably comprising polyether sulfone, glass fibers, cellulose acetate and regenerated cellulose.

According to one embodiment of the invention, the filtering element has a pore size between 0.1 and 10 µm, preferably from 0.2 to 0.8 µm and very preferably 0.45 µm.

According to one embodiment of the invention, the filtering element has a thickness between 0.08 and 0.14 mm.

According to one embodiment of the invention, the filtering element has a cylindrical shape with a diameter adapted to the diameter of a spot of a MALDI-TOF MS analysis plate, and has a flat or hemispherical distal portion.

According to one embodiment of the invention, the filtering element is of convex shape.

According to one embodiment of the invention, the hollow body comprises a tapering portion converging toward the distal end portion of the hollow body.

According to one embodiment of the invention, the distal end portion of the hollow body is cylindrical, flared or flattened.

According to one embodiment of the invention, the proximal end portion of the hollow body is configured for being connected to a vacuum source.

According to one embodiment of the invention, the proximal end portion of the hollow body comprises a retaining part. The retaining part is for example a retaining flange.

According to one embodiment of the invention, the filtering element extends at least partially outside of the hollow body. For example, the filtering element extends or projects from the distal end portion of the hollow body.

According to one embodiment of the invention, the filtering and transfer device comprises an absorbent material arranged in the hollow body.

According to one embodiment of the invention, the absorbent material is at least partly in contact with the filtering element.

According to one embodiment of the invention, the absorbent material is selected from the group comprising cotton, cellulose fiber, polyester, polyethylene agglomerate, an absorbent porous resin, a silica gel, a hydrogel, a molecular sieve, a zeolite or other absorbent materials.

According to one embodiment of the invention, the filtering and transfer device comprises glass beads based on the absorbent material.

According to a particular embodiment of the invention, the absorbent material consists of a monolithic block made from agglomerate of plastic beads (for example of the polyethylene or polyester type) advantageously replacing the assembly of glass beads and absorbent material behind the filtration membrane.

According to one embodiment of the invention, the extraction system further comprises a release well, also called recovery well, mounted, for example removably, on the support bar or inserted directly in the rack.

According to one embodiment of the invention, the release well comprises an inner layer of crosslinked silicone at least partly covering the inside surface of the release well, and contains a predetermined amount of saline solution, for example at 0.45%. The release well may for example contain 250 to 400 µL of saline solution, preferably 320 µL of saline solution at 0.45%.

According to one embodiment of the invention, the at least one washing well contains a washing reagent and the reagent well contains a selective lysis buffer.

According to one embodiment of the invention, the reagent well and the at least one washing well are each sealed by a sealing element.

According to one embodiment of the invention, each sealing element is a sealing film, such as a sealing cover. Each sealing element may for example be made of aluminum.

According to one embodiment of the invention, the extraction system further comprises a sealing device that is movable or deformable between a sealing position in which the sealing device seals the sample well and a release position in which the sealing device releases the sample well at least partly. These arrangements notably make it possible to guarantee closure of the sample well during transport of the support bar or manipulation of a rack equipped with the support bar. They make it possible to guarantee sample integrity as well as the safety of the manipulator throughout any movement in the course of the manipulations (for example from the biological safety cabinet to the instrument).

According to one embodiment of the invention, the sealing device is configured to be moved into the release position when the support bar is positioned on a rack and the rack is loaded into an automatic machine. These arrangements ensure complete opening of the sample well while loading the rack into the automatic machine and complete closure of the sample well during retraction of the rack from the automatic machine, without operator intervention.

According to one embodiment of the invention, the support bar is provided with an identifying code, such as a barcode. These arrangements ensure optimum traceability of the analysis results obtained for each patient.

According to one embodiment of the invention, the support bar is made of plastic.

According to one embodiment of the invention, the hollow body of the filtering and transfer device is made of plastic, and for example of injection-molded crystalline polystyrene or injection-molded polypropylene.

According to one embodiment of the invention, the hollow body of the filtering and transfer device has an inside diameter between 2 mm and 10 mm, and a length between 5 cm and 15 cm. The total length of the filtering and transfer device is for example 9 cm in order to have a sufficient internal volume for containing all of the fluids aspirated during the method and thus constitute a reservoir for retention of said fluids. The distal portion of the filtering and transfer device advantageously has a diameter tapering over some cm of length, allowing it to i) go deeply into the various tubes of the extraction system, ii) adapt to the diameter of the spots of a MALDI-TOF MS analysis plate for the transfer operation.

According to one embodiment of the invention, the hollow body of the filtering and transfer device is rigid or semirigid.

According to one embodiment of the invention, the support bar comprises a plurality of washing wells each configured to contain a washing reagent. The support bar may for example comprise two or three, or even more, washing wells, for which the volume and the composition of the reagents will be adapted if necessary to the application or to the type of sample to be extracted (urine, pus, synovial fluid, etc. previously cultured in liquid growth medium).

According to one embodiment of the invention, the support bar comprises a protecting portion delimiting the at least one protection and retention housing.

According to one embodiment of the invention, the support bar comprises a protection and retention housing, into which the pipetting element and the filtering and transfer device extend at least partially.

According to one embodiment of the invention, the support bar comprises a first protection and retention housing and a second protection and retention housing, into which the pipetting element and the filtering and transfer device respectively extend at least partially.

The present invention further relates to a method for identifying and/or characterizing microorganisms contained in a sample, the identifying and/or characterizing method comprising the following steps:
  providing an extraction system according to the invention, in which the reagent well contains a selective lysis buffer and the at least one washing well contains a washing reagent,
  introducing a predetermined amount of a sample containing microorganisms into the sample well,
  withdrawing a predetermined amount of the selective lysis buffer contained in the reagent well by the pipetting element,
  optionally verifying the presence and the filling level of the sample in the sample well by an optical method,
  introducing the selective lysis buffer withdrawn by the pipetting element into the sample well, and optionally mixing the sample and the selective lysis buffer in said sample well by the pipetting element,
  lysing cells and/or particles that are not micro-organic contained in the sample and/or lysing predetermined microorganisms contained in the sample so as to supply a lysed sample, also called lysate,
  at least partially immersing the filtering and transfer device in the lysed sample contained in the sample well,
  filtering, under aspiration, at least part of the lysed sample through the filtering element,
  capturing and accumulating microorganisms in or on the filtering element,
  at least partially immersing the filtering and transfer device in the washing reagent contained in the at least one washing well,
  washing, in the washing reagent contained in the at least one washing well, the filtering element and the captured and accumulated microorganisms,
  transferring, by the filtering and transfer device, the washed microorganisms onto an analysis support or into a receiver,
  analyzing the transferred microorganisms so as to identify them and/or characterize them.

According to one embodiment of the extraction method, the sample volume introduced into the sample well may vary between 0.5 and 1.2 mL, and the volume of selective lysis buffer withdrawn is then modified to maintain a 2:1 ratio (for example if 1.2 mL of sample is introduced into the sample well, 600 µL of selective lysis buffer is withdrawn).

According to one embodiment of the extraction method, the step of introducing the sample consists of introducing 1 mL of sample into the sample well, the sample preferably being from the positive blood culture, but the method is applicable to the other sterile bodily fluids cultured beforehand in liquid growth medium in order to increase the concentration of the pathogens potentially present before analysis.

According to one embodiment of the extraction method, the step of withdrawing the selective lysis buffer consists of withdrawing 500 µL of selective lysis buffer from the reagent well. This 500 µL is mixed and incubated with the mL of sample present in the sample well, in order to lyse the formed elements of the blood, notably the erythrocytes.

According to one embodiment of the extraction method, the step of mixing the sample and the selective lysis buffer consists of performing several mixing cycles, each mixing cycle consisting of aspirating and discharging a predetermined amount of the mixture contained in the sample well, for example 500 µL (if the sample volume is 1 mL, maintaining a 1:2 ratio), by the pipetting element.

According to one embodiment of the extraction method, the lysis step comprises a step consisting of incubating the mixture for a predetermined time, for example between 1 and 5 minutes, preferably for 2 minutes, at room temperature so as to supply the sample without the elements that are not microorganisms. For example, in the case of a blood culture sample, this step consists of lysing the formed elements of the blood, notably the erythrocytes.

According to one embodiment of the extraction method, the latter comprises a step prior to the step of immersing the filtering and transfer device in the lysed sample, consisting of applying a partial vacuum in the hollow body of the filtering and transfer device.

According to one embodiment of the extraction method, the step of applying a partial vacuum in the hollow body consists of applying a partial vacuum of between −50 mbar and −980 mbar relative to atmospheric pressure, preferably at about −600 mbar relative to atmospheric pressure.

According to one embodiment of the extraction method, the step of filtration with aspiration is carried out for example for 2 minutes.

According to one embodiment of the extraction method, the analysis support is a MALDI-TOF MS analysis plate or an assay plate.

According to one embodiment of the extraction method, the receiver is formed by the release well provided on the support bar or inserted directly in the rack.

According to one embodiment of the extraction method, the latter comprises a step consisting of maintaining the partial vacuum in the hollow body during the various steps of immersion of the filtering and transfer device, the filtration step and the washing step.

According to one embodiment of the extraction method, the washing step comprises the following step:

displacing for a predetermined time, for example between 30 seconds and 5 minutes, preferably for 2 minutes, the filtering and transfer device in the at least one washing well, for example with a reciprocating movement in Z.

According to one embodiment of the extraction method, the step of displacing the filtering and transfer device in the at least one washing well consists of performing several cycles of displacement of the filtering and transfer device in the at least one washing well. Advantageously, the filtering and transfer device is withdrawn completely out of the at least one washing well with each cycle of displacement, for example at a frequency of about 0.5 to 2 Hz, preferably 1 Hz.

According to one embodiment of the extraction method, the latter comprises a collecting step carried out between the washing step and the transfer step and comprising the following steps:

withdrawing the filtering and transfer device out of the washing reagent contained in the at least one reagent well, and displacing the distal end portion of the hollow body transversely in the direction of extension of the hollow body in such a way that the distal end portion of the hollow body comes into contact with an inside wall of the at least one washing well.

These arrangements make it possible to collect, in the at least one washing well, residual washing drops that are present at the level of the distal end portion of the filtering and transfer device, and therefore avoid subsequent deposition of an excessive amount of liquid on the analysis support.

According to one embodiment of the extraction method, the collecting step comprises a step consisting of holding the distal end portion of the hollow body against the inside wall of the at least one washing well for a predetermined time, for example for 5 to 20 seconds, preferably 10 seconds. Advantageously, the partial vacuum in the hollow body is maintained during the maintaining step in order to aspirate some or all of the residual liquid attached to the distal portion of the filtering and transfer device.

According to one embodiment of the extraction method, the latter comprises a step prior to the transfer step, and advantageously subsequent to the step of holding the distal end portion of the hollow body against the inside wall of the at least one washing well, and consisting of placing the hollow body at atmospheric pressure or slightly increased pressure.

According to one embodiment of the extraction method, the step of immersing the filtering and transfer device in the washing reagent contained in the at least one washing well consists of plunging the filtering and transfer device more deeply, for example 1 to 3 mm deeper, than in the lysed sample contained in the sample well.

According to one embodiment of the extraction method, the transfer step comprises a step consisting of depositing, by the filtering and transfer device, at least one part of the washed microorganisms on one or more predetermined locations, also called spots, of a MALDI-TOF MS analysis plate.

According to one embodiment of the extraction method, the latter further comprises the following steps carried out before the analysis step:

controlled drying of the various spots of the MALDI-TOF MS analysis plate on which microorganisms were deposited, optionally taking an image of the spots at which microorganisms were deposited, for example under two different illuminations, adding a predetermined amount of matrix, for example from 0.5 to 2 µL, preferably 1 µL, on each spot of the MALDI-TOF MS analysis plate where microorganisms have been deposited, controlled drying of the various spots of the MALDI-TOF MS analysis plate on which the matrix was deposited, optionally taking an image of the spots on which the matrix was deposited, for example under two different illuminations.

According to one embodiment of the extraction method, the matrix is a DHB matrix, i.e. a 2,5-dihydroxybenzoic acid, an HCCA matrix, i.e. an α-cyano-4-hydroxycinnamic acid, or an SA matrix, i.e. a sinapinic (3,5-dimethoxy-4-hydroxycinnamic) acid.

According to one embodiment of the extraction method, the latter comprises a step carried out prior to the step of adding the matrix and consisting of adding a predetermined amount of formic acid, for example from 0.5 to 2 µL, preferably 0.5 to 1 µL, on each spot of the MALDI-TOF MS analysis plate where microorganisms have been deposited. These arrangements notably make it possible to improve the results of identification for Gram-positives and yeasts.

According to one embodiment of the extraction method, the step of depositing the washed microorganisms on one or more predetermined spots of the MALDI-TOF MS analysis plate comprises a step consisting of applying the filtering element against the or each predetermined spot of the MALDI-TOF MS analysis plate with a controlled force of application between 100 grams and 1 kg per filtration device, preferably 600 grams.

According to one embodiment of the extraction method, the step of depositing the washed microorganisms on one or more predetermined spots of the MALDI-TOF MS analysis plate comprises a step consisting of dabbing the filtering element one or more times on the or each predetermined spot of the MALDI-TOF MS analysis plate. These arrangements make it possible to deposit a sufficient amount of microorganisms on each predetermined spot of the MALDI-TOF MS analysis plate.

According to one embodiment of the extraction method, a step of taking images of the spots on the MALDI-TOF MS analysis plate may optionally be carried out; depending on the control requirements, these steps of taking images may be carried out immediately after transferring the microorganisms or after depositing the formic acid and matrix reagents in order to verify that a deposit is actually present. Preferably, these steps of taking images are performed after each of the drying steps in order to verify the quality and quantity of the deposit of the microorganisms, good interaction between formic acid and the deposit of microorganisms (presence of a halo), good distribution and crystallization of the matrix with the microorganisms deposited on the MALDI-TOF MS analysis plate.

According to one embodiment of the extraction method, the dabbing step consists of dabbing the filtering element several times, for example between 3 and 7 times, on the or each predetermined spot of the MALDI-TOF MS analysis plate at a frequency of dabbing between 0.5 and 10 Hz.

According to one embodiment of the extraction method, the preceding step may be combined with and linked to a sequence of pressurizing the hollow body of the filtering and transfer device in order to facilitate transfer of the microorganisms from the filtering membrane to the surface of the MALDI-TOF MS analysis plate.

According to one embodiment of the extraction method, the analysis step comprises a step consisting of performing a mass spectrometry analysis of the MALDI-TOF type of the microorganisms transferred, and for example microorganisms deposited on a MALDI-TOF MS analysis plate.

According to one embodiment of the extraction method, the analysis step comprises a step consisting of inserting the analysis support in a mass spectrometer.

According to one embodiment of the extraction method, the washing step comprises a step consisting of separating, isolating or purifying the microorganisms captured and accumulated in the filtering element, for example by facilitating evacuation of the other components that may be present in the lysed sample, such as cellular debris, elements that are not micro-organic, and which would be likely to interfere with the subsequent analysis of the microorganisms.

According to one embodiment of the extraction method, the latter comprises a step, at the beginning of the method, consisting of piercing sealing films of the at least one washing well and of the reagent well by the pipetting element. These arrangements notably make it possible to create an opening large enough for the filtering and transfer device to be able to penetrate into the washing well or the various washing wells without damaging the filtering element.

According to one embodiment of the extraction method, the piercing step consists of piercing the at least one washing well and then the reagent well by a vertical and optionally horizontal movement of the pipetting element.

According to one embodiment of the extraction method, the latter comprises a step consisting of detecting an identifying code provided on the extraction bar in order to combine it with the identifying code provided on the container containing the sample initially (for example a vial of positive blood culture) and thus ensure optimum traceability of the analysis results.

According to one embodiment of the extraction method, the latter comprises a step carried out after the step of depositing the microorganisms on the MALDI-TOF MS analysis plate and before the step of adding the matrix and consisting of incubating the MALDI-TOF MS analysis plate at between 40 and 80° C., for example at 50° C., for a predetermined time, for example between 2 and 6 minutes, preferably 4 minutes, so as to dry or evaporate any residual washing reagent present on the or each predetermined spot.

According to one embodiment of the extraction method, the latter comprises a step carried out after the step of adding formic acid and consisting of incubating the MALDI-TOF MS analysis plate at between 40 and 80° C., for example at 45° C. or at 55° C., for a predetermined time, for example between 5 and 7 minutes, preferably 6 minutes, so as to speed up the evaporation of the drops of formic acid, while ensuring a sufficient contact time of the formic acid with the microorganisms present on the MALDI-TOF MS analysis plate to guarantee effective lysis of the membranes of the microorganisms.

According to one embodiment of the extraction method, the latter comprises a step carried out after the step of adding the matrix and consisting of incubating the MALDI-TOF MS analysis plate at between 40 and 80° C. for a predetermined time, for example between 1 and 3 minutes, preferably 2 minutes.

According to one embodiment of the extraction method, the step of depositing the microorganisms on the predetermined spot or spots of the MALDI-TOF MS analysis plate comprises a step consisting of vibrating the filtering and transfer device, and more particularly of vibrating the filtering and transfer device at least during contact of the filtering element on the or each predetermined spot of the MALDI-TOF MS analysis plate. These arrangements make it possible to improve the transfer of the microorganisms (quantity and reproducibility) from the filtering element to the MALDI-TOF MS analysis plate.

According to one embodiment of the extraction method, the step of vibrating the filtering and transfer device consists of applying a vibration of between 0.1 and 200 Hz, for example between 10 and 100 Hz, preferably 50 Hz, for a predetermined time, and for example between 1 and 5 seconds, preferably for 2 seconds.

According to one embodiment of the extraction method, the transfer step comprises a step consisting of resuspending the washed microorganisms in a saline solution, for example at 0.45%, contained in the release well.

According to one embodiment of the extraction method, the resuspension step comprises the following steps:
 at least partially immersing the filtering and transfer device in the saline solution contained in the release well,
 repeatedly contacting, for example by a reciprocating vertical movement of the release well and/or of the filtering and transfer device, the filtering element with the inner layer of crosslinked silicone at least partly covering the inside surface of the release well for a predetermined time, and advantageously at a predetermined frequency.

According to one embodiment of the extraction method, the latter comprises a step consisting of measuring the optical density of the saline solution contained in the release well and containing the washed microorganisms. Measurement of optical density may for example be carried out in the release well above the inner layer of crosslinked silicone or directly in the pipetting element.

According to one embodiment of the extraction method, the latter comprises a step consisting of adjusting, for example to 0.5 µF, the concentration of microorganisms in the saline solution contained in the release well by adding saline solution to the release well. This step may advantageously be carried out automatically by controlling the addition of saline solution calculated from the measurement of optical density performed in the release well.

According to one embodiment of the extraction method, the latter comprises the following steps:
 withdrawing, from the release well, a predetermined amount of the saline solution containing the microorganisms previously adjusted to a value of optical density of 0.5 µF, for example between 100 and 300 µL and advantageously 145 or 285 µL depending on the type of microorganisms (Gram-positive or Gram-negative),
 placing the saline solution withdrawn in an analysis container containing a predetermined amount of saline solution, for example at 0.45%, in order to obtain a predetermined concentration of microorganisms, for example of 0.05 or 0.025 µF depending on the type of microorganisms (for example Gram-negative, Gram-positive or yeasts), for preparing to start an antibiogram analysis directly from the positive blood culture without going via the step of culturing on a medium.

According to one embodiment of the extraction method, the analysis container contains between 2 and 4 mL, preferably 3 mL of saline solution at 0.45%.

According to one embodiment of the extraction method, the analysis container is mounted, for example removably, on the support bar. Advantageously, the analysis container is arranged near the release well.

According to one embodiment of the extraction method, the step of analysis of the microorganisms that have been transferred consists of performing an antibiogram analysis. Advantageously, the analysis step comprises a step consisting of transferring a predetermined amount of the consumable, contained in the analysis container and containing the transferred microorganisms, into an antibiogram analyzer, and performing an antibiogram analysis on the transferred consumable.

According to a variant embodiment of the extraction method, the resuspension step comprises a step consisting of rubbing the filtering element on a nylon grating wetted beforehand with a saline solution at 0.45%.

According to another variant embodiment of the extraction method, the resuspension step comprises the following steps:
  at least partially introducing the filtering and transfer device into the release well,
  cutting out the filtering element, for example by a cutting component inserted in the release well,
  releasing the filtering element in the saline solution contained in the release well,
  causing movement of the release well for a predetermined time, for example for 30 seconds to 1 minute, so as to release the microorganisms from the filtering element and resuspend them in the saline solution.

According to one embodiment of the extraction method, the cutting step comprises a step consisting of rotating the release well relative to the filtering and transfer device, for example through a half-turn.

According to one embodiment of the extraction method, the latter further comprises the following steps:
  providing a rack,
  positioning the support bar on the rack.

According to one embodiment of the extraction method, the step of positioning the support bar comprises a step consisting of automatically moving the sealing device from the sealing position to the release position.

According to one embodiment of the extraction method, the latter comprises a step consisting of providing an automatic machine comprising a manipulation part configured for grasping/releasing and moving the pipetting element mounted on the support bar and for grasping/releasing and moving the filtering and transfer device mounted on the support bar.

According to one embodiment of the extraction method, the manipulation part of the automatic machine provided is configured for moving respectively the pipetting element and the filtering and transfer device according to Cartesian movements.

According to one embodiment of the extraction method, the automatic machine provided comprises a receiving zone configured for receiving a rack equipped with the support bar.

In any case, the invention will be better understood with the aid of the description given hereunder, referring to the appended schematic drawings showing, as nonlimiting examples, two embodiments of this extraction system.

Figure 1:
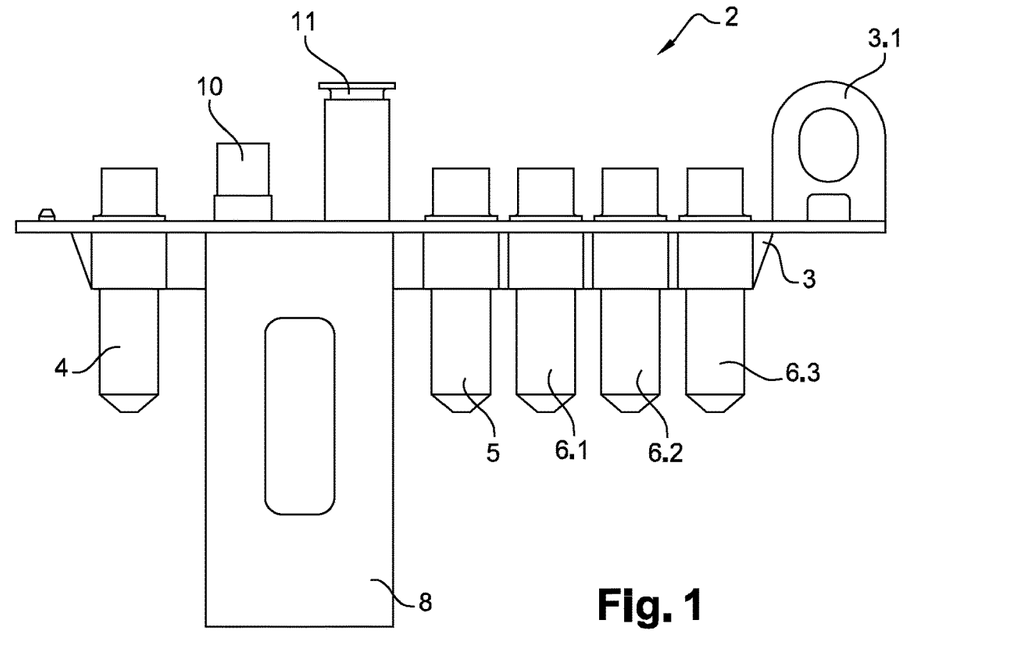
FIG. 1 is a side view of an extraction system according to a first embodiment of the invention.
Figure 2:
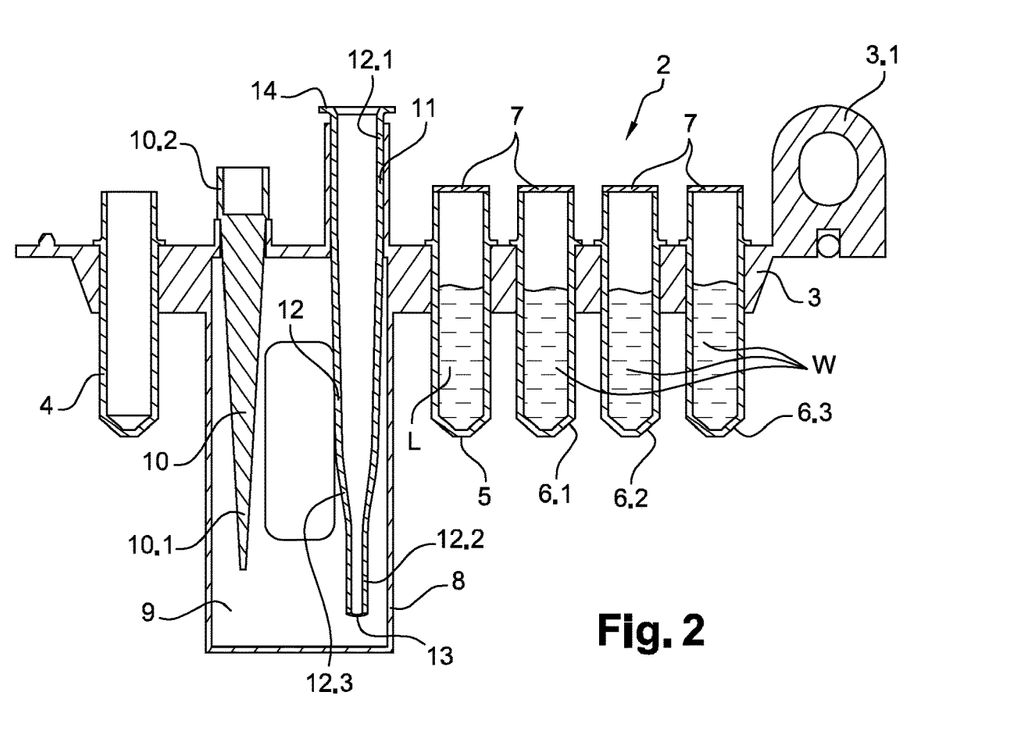
FIG. 2 is a sectional view of the extraction system in FIG. 1.
Figure 3:
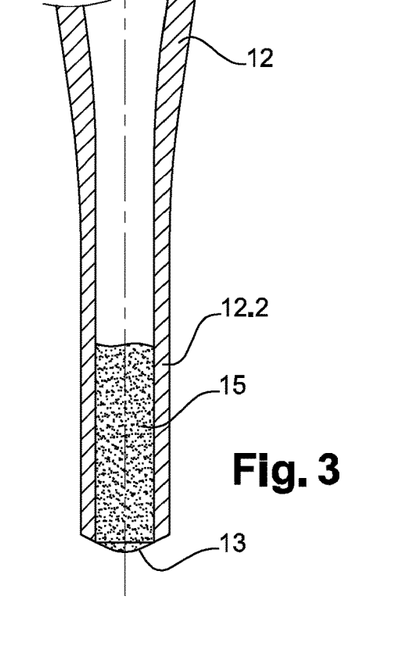
FIG. 3 is a partial sectional view of a distal end portion of a filtering and transfer device of the extraction system in FIG. 1.

FIGS. 1 to 3 show an extraction system 2, for extracting microorganisms contained in a sample, according to a first embodiment of the invention. The sample may for example be a microbiological culture, such as a positive blood culture. The sample may moreover be a body fluid, such as cerebrospinal fluid, synovial fluid, urine or pus that has been cultured beforehand in a suitable liquid culture medium, in order to increase the concentration of microorganisms per mL.

The extraction system 2 comprises a support bar 3 made for example of plastic, and advantageously provided with an identifying code, such as a barcode.

Figure 6:
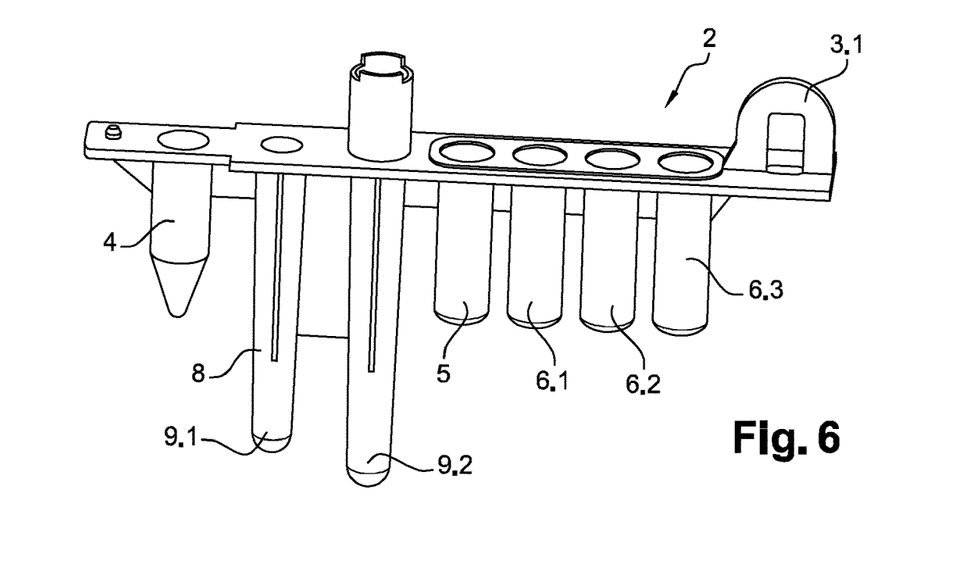
FIG. 6 is a perspective partial view of an extraction system according to a second embodiment of the invention.

As shown more particularly in FIG. 2, the support bar 3 notably comprises a sample well 4 configured to receive a sample containing microorganisms, a reagent well 5 containing a selective lysis buffer L, and one or more washing wells each containing a washing reagent W. According to the embodiment shown in FIGS. 1 to 3, the sample well 4, the reagent well 5 and the washing well or wells are mounted on the support bar 3. However, according to another embodiment of the extraction system 2, the support bar 3, the sample well 4, the reagent well 5 and the washing well or wells could be produced directly by molding, and notably by injection molding (see FIG. 6).

According to the embodiment shown in FIGS. 1 to 3, the support bar 3 comprises a washing well 6.1 containing a washing reagent having a formulation identical to the formulations described in document WO2013/016211, a washing well 6.2 containing a washing reagent having a formulation identical to the formulations described in document WO2013/016211, and a washing well 6.3 containing for example sterile deionized water. Each of the washing wells may for example contain 1400 μL of the respective washing reagent.

According to one embodiment of the invention, the selective lysis buffer L contained in the reagent well 5 has a formulation identical to the formulations described in document WO2013/016211.

The sample well 4, the reagent well 5 and the washing well or wells 6.1, 6.2, 6.3 are advantageously aligned in the direction of extension of the support bar 3. Advantageously, the reagent well 5 and the washing well or wells 6.1, 6.2, 6.3 are sealed with respective sealing covers 7, consisting for example of an aluminum/polyethylene composite heat-sealed to the surface of the reagent and washing wells.

The support bar 3 also comprises a gripping part 3.1 facilitating manipulation thereof by an operator.

The support bar 3 further comprises a protecting portion 8 delimiting a protection and retention housing 9 which is open at the top and whose function will be stated below. According to the embodiment shown in FIGS. 1 to 3, the protecting portion 8 is arranged between the sample well 4 and the reagent well 5. This position is provided in order to minimize the risks of soiling, during movement of the pipetting element above the support bar 3.

The extraction system 2 further comprises a pipetting element 10, for example made of plastic, removably mounted on the support bar 3, and extending at least partially into the protection and retention housing 9. According to the embodiment shown in FIGS. 1 to 3, the pipetting element 10 comprises a tapered distal end portion 10.1 extending into the protection and retention housing 9, and a proximal end portion 10.2 configured for being connected to a vacuum source or a volume displacement device, such as an electronically controlled syringe. Advantageously, the protection and retention housing 9 is configured for retaining drops of liquid, such as drops of sample or of reagents, able to flow by gravity from the tapered distal end portion 10.1 of the pipetting element 10. Once the pipetting operations have been carried out, the pipetting element 10 is repositioned in its housing in the extraction bar 3.

The extraction system 2 also comprises a filtering and transfer device 11 configured to capture and accumulate microorganisms contained in the sample and to transfer the captured and accumulated microorganisms notably to an analysis support or receiver. The filtering and transfer device 11 is removably mounted on the support bar 3, and extends at least partially into the protection and retention housing 9.

Figure 7:
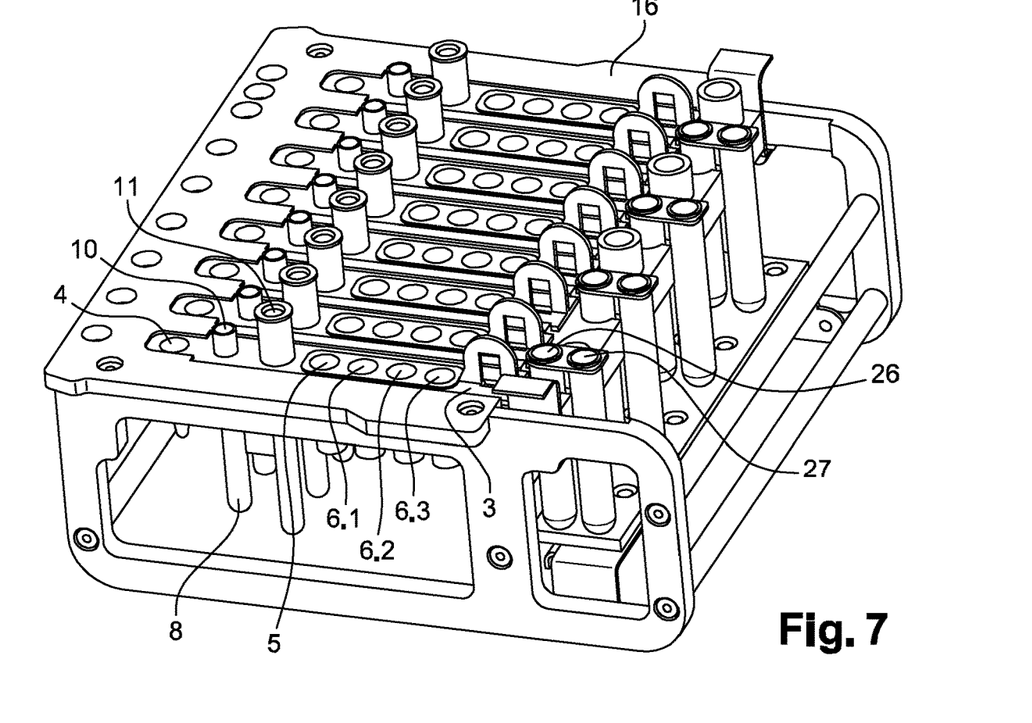
FIG. 7 is a perspective view of a rack equipped with a plurality of extraction systems from FIG. 6 and moreover with additional containers.
Figure 8:
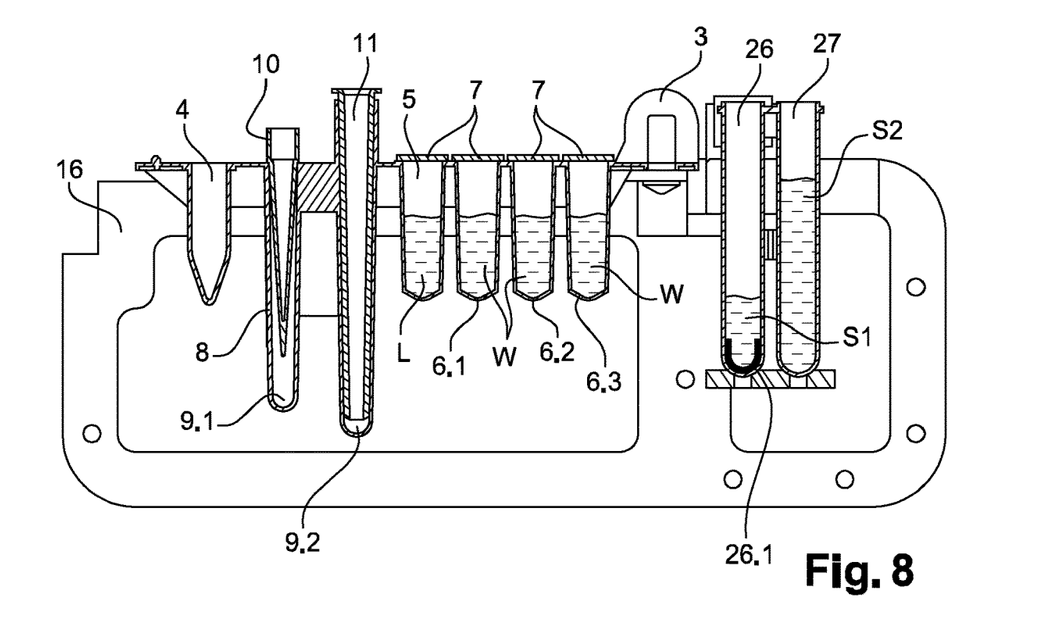
FIG. 8 is a sectional view of the rack in FIG. 7, but with addition of sealing elements configured for sealing a reagent well and with washing wells of an extraction system provided on the rack.

The filtering and transfer device 11 more particularly comprises a hollow body 12 having an elongated shape and comprising a proximal end portion 12.1 and a distal end portion 12.2, and a filtering element 13 fixed to the distal end portion 12.2 of the hollow body 12, for example by welding and notably by heat-sealing or by ultrasonic welding, or else with solvent. The distal end portion 12.2 of the hollow body 12 and the filtering element 13 extend into the protection and retention housing 9, and the protection and retention housing 9 is configured for retaining drops of sample or of reagents able to flow by gravity from the filtering and transfer device 11. However, according to another embodiment of the extraction system 2 (see FIGS. 6 to 8), the protecting portion 8 could comprise two protection and retention housings 9.1, 9.2, in which the distal end portion 10.1 of the pipetting element 10 and the distal end portion 12.2 of the hollow body 12 of the filtering and transfer device 11, respectively, would be mounted.

The hollow body 12 of the filtering and transfer device 11 is advantageously rigid or semirigid, and may be made of plastic, and for example of injection-molded crystalline polystyrene or of injection-molded polypropylene.

According to the embodiment shown in FIGS. 1 to 3, the hollow body 12 comprises a tapered intermediate portion 12.3 converging toward the distal end portion 12.2 of the hollow body 12, and the distal end portion 12.2 is cylindrical. However, the hollow body 12 could have a different shape, and the distal end portion 12.2 could notably be tapered. For example, according to the embodiment shown in FIG. 8, the hollow body 12 has a cross section that decreases gradually from the proximal end portion 12.1 to the distal end portion 12.2.

It should be noted that the proximal end portion 12.1 of the hollow body 12 is configured for being connected to the source of partial vacuum, and may for example be provided with a retaining flange 14. This retaining flange 14 also serves as a reference plane for accurately positioning the filtering and transfer device in Cartesian coordinates during the steps of transfer onto the MALDI-TOF MS analysis plate.

As shown more particularly in FIG. 3, the filtering element 13 extends at least partially outside the hollow body 12. For example, the filtering element 13 projects from the distal end portion 12.2 of the hollow body 12. According to the embodiment shown in FIGS. 1 to 3, the filtering element 13 is of convex shape, and more particularly is dome-shaped. However, the filtering element 13 could have some other shape, and for example be flat and disk-shaped. The filtering element 13 could also be of cylindrical shape and have a flat or hemispherical distal portion. The filtering element 13 could moreover have a diameter adapted to the diameter of a spot of a MALDI-TOF MS analysis plate. The filtering element 13 could moreover be made in situ in the hollow body 12.

The filtering element 13 advantageously has a pore size between 0.1 and 10 μm, and for example of about 0.45 μm, and is more particularly configured for retaining at least one portion of the microorganisms contained in the sample and for allowing other elements contained in the sample to pass through, such as elements that are not micro-organic, for example cellular debris and the formed elements of the blood previously lysed with the lysis reagent.

The filtering and transfer device 11 may further comprise an absorbent material 15 arranged in the hollow body 12 and at least partly in contact with the filtering element 13. The absorbent material 15 may for example be selected from the group comprising cotton, cellulose fiber, aggregate of polyethylene beads, polyester, an absorbent resin, a silica gel, a hydrogel, a molecular sieve, a zeolite or other absorbent materials.

A first method for identifying and/or characterizing microorganisms contained in a sample using an extraction system 2 according to the first embodiment of the invention will now be described.

The first method of identification and/or characterization comprises the following steps:
- detecting the identifying code that is provided on the container containing the sample initially (for example a vial of positive blood culture),
- loading the support bar 3 on a rack 16 (see FIG. 4),
- detecting the identifying code that is provided on the extraction bar 3,
- placing a predetermined amount, for example 1 mL, of a sample containing microorganisms, for example a positive blood culture, in the sample well 4 of the extraction system 2,
- loading the rack 16 equipped with the support bar 3 in an automatic machine 17 (see FIG. 5) comprising a manipulating part 18 configured for grasping/releasing and moving the pipetting element 10 mounted on the support bar 3 according to Cartesian movements and for grasping/releasing and moving the filtering and transfer device 11 mounted on the support bar 3 according to Cartesian movements, the manipulating part 18 being configured for example for moving the pipetting element 10 and the filtering and transfer device 11 of the or of each support bar 3 loaded on the rack 16, along the Y axis and along the Z axis of a Cartesian system, and comprising for example several first manipulating elements 18.1 each configured for grasping/releasing a respective pipetting element 10 and several second manipulating elements 18.2 each configured for grasping/releasing a respective filtering and transfer device 11, the first manipulating elements 18.1 being for example aligned according to a first direction of alignment and the second manipulating elements 18.2 being for example aligned according to a second direction of alignment approximately parallel to the first direction of alignment, optionally, by a camera 19 belonging to the automatic machine 17, taking images of predetermined spots 21 of a MALDI-TOF MS mass spectrometry analysis plate 22 arranged on a support module 23 of the automatic machine 17, before making deposits on these predetermined spots 21, the support module 23 being for example movable along the X axis of a Cartesian system, grasping the pipetting element 10 mounted on the support bar 3 by the manipulating part 18, piercing the sealing films 7 of the washing wells 6.1, 6.2, 6.3 and of the reagent well 5 on progressing from the washing well 6.3 to the reagent well, for example by the pipetting element 10, withdrawing a predetermined amount, for example 500 µL, of the selective lysis buffer L contained in the reagent well 5 by the pipetting element 10, placing, by the pipetting element 10, the withdrawn selective lysis buffer in the sample well 4, mixing the sample and the selective lysis buffer contained in the sample well 4 by the pipetting element 10, repositioning the pipetting element 10 on the support bar 3, incubating the mixture for a predetermined time, for example between 1 and 5 minutes, preferably for 2 minutes, at room temperature so as to lyse cells and/or particles that are not micro-organic contained in the sample and/or to lyse predetermined microorganisms contained in the sample in order to supply a lysed sample, also called lysate, grasping the filtering and transfer device 11 mounted on the support bar 3 by the manipulating part 18, applying and maintaining a partial vacuum between −50 mbar and −980 mbar relative to atmospheric pressure, preferably at about −600 mbar relative to atmospheric pressure, in the hollow body 12 of the filtering and transfer device 11, the partial vacuum being generated by a pump 20 belonging to the automatic machine 17 and connected fluidically to the manipulating part 18, the pump 20 being for example a vacuum and booster pump, and which may for example be connected to a vacuum ballast and a pressure ballast, at least partially immersing the distal end portion 12.2 of the filtering and transfer device 11 in the lysed sample contained in the sample well 4, filtering with aspiration, for example for 2 minutes, at least part of the lysed sample through the filtering element 13, capturing and accumulating microorganisms in the filtering element 13, at least partially immersing the distal end portion 12.2 of the filtering and transfer device 11 in the washing reagent contained in the washing well 6.1, washing the filtering element 13 and the captured and accumulated microorganisms, in the washing reagent contained in the washing well 6.1, for example by a cycle of reciprocating vertical movement for 30 s to 2 min, preferably 1 min, at least partially immersing the distal end portion 12.2 of the filtering and transfer device 11 in the washing reagent contained in the washing well 6.2, washing the filtering element 13 and the captured and accumulated microorganisms in the washing reagent contained in the washing well 6.2, for example by a cycle of reciprocating vertical movement for 30 s to 2 min, and then statically for 30 s to 5 min, preferably 3 min, at least partially immersing the distal end portion 12.2 of the filtering and transfer device 11 in the washing reagent contained in the washing well 6.3, washing the filtering element 13 and the captured and accumulated microorganisms in the washing reagent contained in the washing well 6.3, for example by a cycle of reciprocating vertical movement for 30 s to 2 min, and then statically for 30 s to 5 min, preferably 3 min, retracting the distal portion of the filtering and transfer device 11 out of the washing reagent contained in the washing well 6.3 and moving the distal end portion 12.2 of the hollow body 12 transversely in the direction of extension of the hollow body 12 in such a way that the distal end portion of the hollow body 12 comes into contact with the inside wall of the washing well 6.3 and so that the residual washing drops that are present at the level of the distal end portion 12.2 of the hollow body 12 are collected in the washing well 6.3, holding the distal end portion 12.2 of the hollow body 12 against the inside wall of the washing well 6.3 for a predetermined time, for example for 5 to 15 seconds, while maintaining the level of partial vacuum, returning the hollow body 12 of the filtering and transfer device 11 to atmospheric pressure or slight overpressure (50 to 200 mbar) for the time required for the next step, depositing, by the filtering and transfer device 11, at least one part of the washed microorganisms on one or more predetermined locations 21, also called spots, of the MALDI-TOF MS analysis plate 22 (see FIG. 11), repositioning the filtering and transfer device 11 on the support bar 3, incubating the MALDI-TOF MS analysis plate 22 at between 40 and 80° C., for example at 45° C. or at 55° C., for a predetermined time, for example between 2 and 6 minutes, preferably 4 minutes, so as to dry or evaporate any residual washing reagent present on the or each predetermined spot 21 of the MALDI-TOF MS analysis plate 22, for which purpose the support module 23 may be provided with at least one heating element 24, optionally, taking an image of the predetermined spots 21 by the camera 19, optionally, adding a predetermined amount of formic acid, for example from 0.5 to 1 µL, preferably 0.5 µL, on each spot 21 of the MALDI-TOF MS analysis plate 22 where microorganisms have been deposited, for example using a pipetting device (not shown in the figures) belonging to the automatic machine 17 and movable for example along the Y axis and along the Z axis of a Cartesian system, incubating the MALDI-TOF MS analysis plate at between 40 and 80° C., for example at 45° C. or at 55° C., for a predetermined time, for example between 5 and 7 minutes, preferably 6 minutes so as to dry each predetermined spot 21 of the MALDI-TOF MS analysis plate 22, optionally, taking an image of the spots 21 by the camera 19, adding a predetermined amount of matrix, for example from 0.5 to 2 µL, preferably 1 µL of HCCA matrix, on each spot 21 of the MALDI-TOF MS analysis plate 22 where microorganisms have been deposited, for example by the pipetting device, incubating the MALDI-TOF MS analysis plate 22 at between 40 and 80° C. for a predetermined time, for example between 1 and 3 minutes, preferably 2 minutes, optionally, taking an image of the spots 21 by the camera 19, inserting the MALDI-TOF MS analysis plate 22 in a mass spectrometer, and performing a mass spectrometry analysis of the microorganisms transferred onto each predetermined spot 21 of the MALDI-TOF MS analysis plate 22 so as to identify and/or characterize the microorganisms.

According to one embodiment of the first extraction method, each washing step comprises a step consisting of moving, for a predetermined time, for example between 30 seconds and 5 minutes, preferably for 2 minutes, the filtering and transfer device 11 in the respective washing well, for example with a reciprocating movement in Z. Advantageously, each step of moving the filtering and transfer device 11 consists of performing several cycles of vertical displacement of the filtering and transfer device 11 in the respective washing well. Advantageously, the filtering and transfer device 11 is withdrawn from the respective washing well completely at each cycle of displacement, for example at a frequency of about 0.5 to 2 Hz, and preferably 1 Hz.

According to one embodiment of the first extraction method, the step of immersing the filtering and transfer device 11 in the washing reagent contained in the washing well 6.1 consists of plunging the filtering and transfer device 11 more deeply, for example from 1 to 3 mm deeper, than in the lysed sample contained in the sample well 4, the step of immersing the filtering and transfer device 11 in the washing reagent contained in the washing well 6.2 consists of plunging the filtering and transfer device 11 more deeply, for example from 1 to 3 mm deeper, than in the washing reagent contained in the washing well 6.1, and the step of immersing the filtering and transfer device 11 in the washing reagent contained in the washing well 6.3 consists of plunging the filtering and transfer device 11 more deeply, for example from 1 to 3 mm deeper, than in the washing reagent contained in the washing well 6.2.

Figure 11:
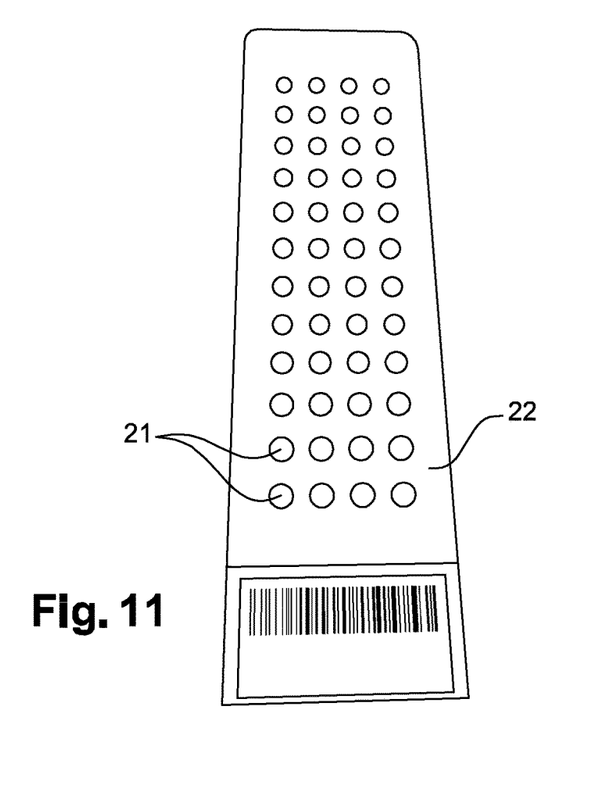
FIG. 11 is a perspective view of a MALDI-TOF MS analysis plate.

According to one embodiment of the first extraction method, the step of depositing the washed microorganisms on one or more predetermined spots 21 of the MALDI-TOF MS analysis plate 22 comprises a step consisting of dabbing the filtering element 13 several times, for example between 3 and 7 times, on the or each predetermined spot 21 of the MALDI-TOF MS analysis plate 22 with a force of application between 100 grams and 1 kg, preferably 600 grams, and according to a frequency of dabbing between 0.5 and 10 Hz. These arrangements make it possible to deposit a sufficient amount of microorganisms on each predetermined spot of the MALDI-TOF MS analysis plate 22.

According to one embodiment of the first extraction method, the step of depositing the microorganisms on the predetermined spot or spots 21 of the MALDI-TOF MS analysis plate 22 comprises a step consisting of vibrating the filtering and transfer device 11 at least during contact of the filtering element 13 on the or each predetermined spot of the MALDI-TOF MS analysis plate. These arrangements make it possible to improve the transfer of the microorganisms (quantity and reproducibility) from the filtering element 13 to the MALDI-TOF MS analysis plate, notably for the microorganisms that are difficult to detach and identify or are known to generate low concentrations while they grow in a blood culture flask.

According to one embodiment of the first extraction method, the step of vibrating the filtering and transfer device 11 consists of applying a vibration of between 0.1 and 200 Hz, for example between 10 and 100 Hz, preferably 50 Hz, to the filtering and transfer device 11 for a predetermined time, and for example for 2 seconds.

According to one embodiment of the first extraction method, the step of depositing the microorganisms on the predetermined spot or spots 21 of the MALDI-TOF MS analysis plate 22 comprises a step consisting of applying a cycle of increased pressure (adjustment of the pressure, of the pulse number, of the cyclic ratio or of the duration of the pressure pulse cycle), relative to atmospheric pressure, in the hollow body 12 of the filtering and transfer device 11 during contact of the filtering element 13 on the or each predetermined spot 21 of the MALDI-TOF MS analysis plate 22 or between two contacts of the filtering element 13 on the MALDI-TOF MS analysis plate 22. These arrangements make it possible to improve the transfer of the microorganisms from the filtering element 13 to the MALDI-TOF MS analysis plate 22.

According to one embodiment of the first extraction method, the step of mixing the sample and the selective lysis buffer consists of performing several mixing cycles, each mixing cycle consisting of aspirating and discharging a predetermined amount of the mixture contained in the sample well 4, for example 500 µL, by the pipetting element.

According to one embodiment of the first extraction method, the latter comprises a step carried out prior to the step of adding the matrix and consisting of adding a predetermined amount of formic acid, for example from 0.5 to 2 µL, preferably 0.5 to 1 µL, on each spot of the MALDI-TOF MS analysis plate where microorganisms have been deposited. These arrangements notably make it possible to improve the results of identification for the Gram-positive bacteria and the yeasts.

According to one embodiment of the first extraction method, the latter comprises a step carried out after the step of adding formic acid and consisting of incubating the MALDI-TOF MS analysis plate 22 at between 40 and 80° C., for example at 45° C. or at 55° C., for a predetermined time, for example between 5 and 7 minutes, preferably 6 minutes, so as to speed up the evaporation of the drops of formic acid, while ensuring sufficient contact of the formic acid with the microorganisms present on the MALDI-TOF MS analysis plate to guarantee effective lysis.

According to one embodiment of the first extraction method, the latter comprises a step of taking an image, for example under two different types of illumination, of the predetermined spots at different steps of the method and preferably after each drying step (vacuum drying, microorganisms, formic acid, matrix) for process control at each step (notably the following points: correct transfer of the microorganisms, localization and correct mixing of the formic acid and of the matrix with the deposited microorganisms, satisfactory level of crystallization of the matrix with the microorganisms).

According to one embodiment of the first extraction method, the latter comprises a step of taking an image of the rack after insertion in the automatic machine using an inexpensive camera (webcam) incorporated in the automatic machine. This taking of an image makes it possible, with suitable image processing, to verify the position of the rack, the number and the proper insertion of the bars, and proper presence of the pipetting and filtering elements before starting the extraction cycle.

A second method for identifying and/or characterizing microorganisms contained in a sample using an extraction system 2 according to the first embodiment of the invention will now be described.

Figure 4:
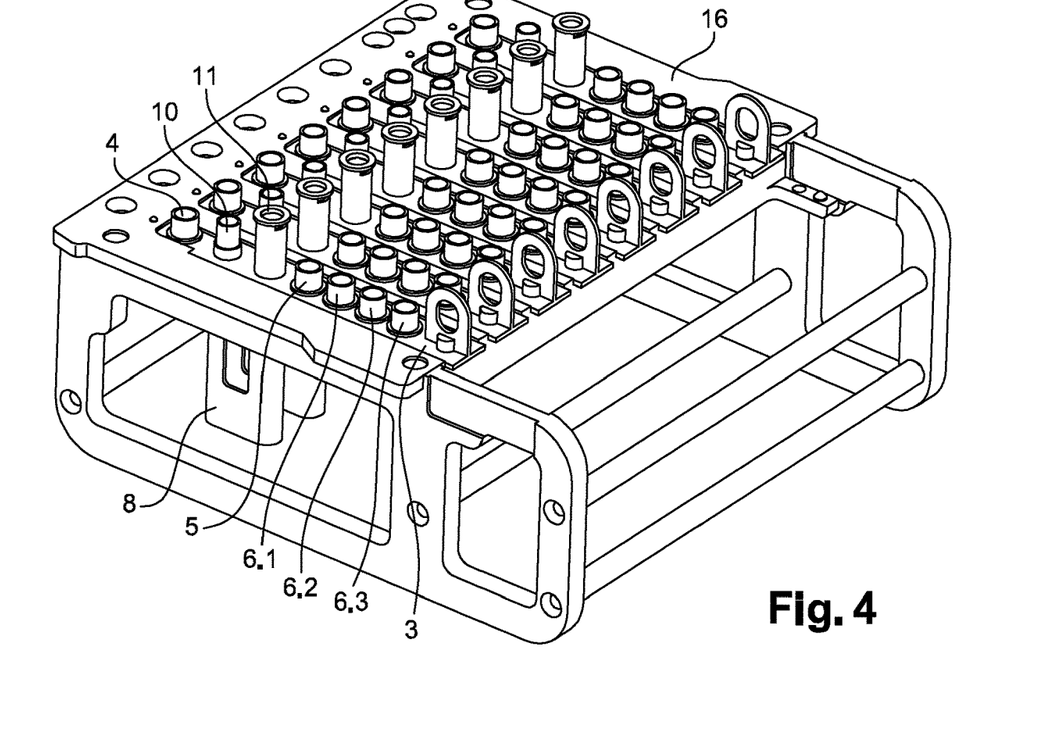
FIG. 4 is a perspective view of a rack equipped with a plurality of extraction systems from FIG. 1.
Figure 5:
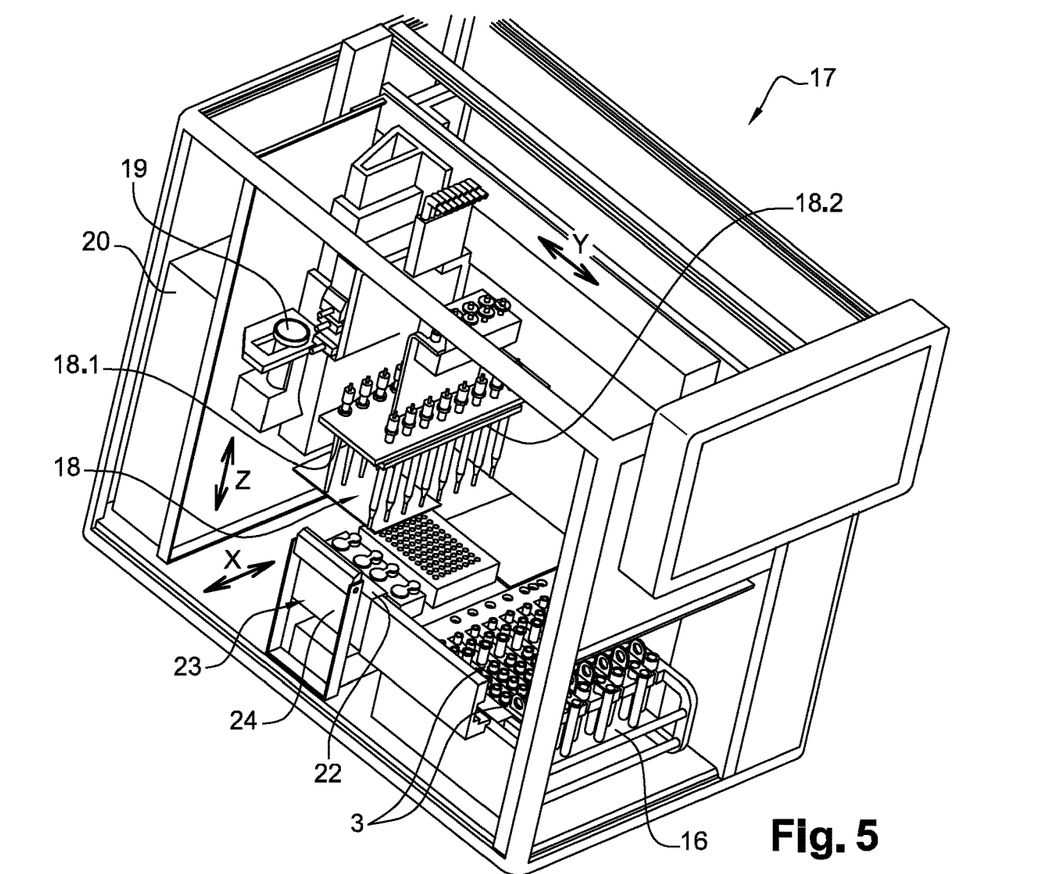
FIG. 5 is a perspective view of an automatic machine equipped with the rack in FIG. 4.

The second method of identification and/or characterization comprises the following steps:
- loading the support bar 3 and a release well 26 on a rack 16,
- detecting the identifying code that is provided on the extraction bar 3 and detecting the identifying code that is provided on the container containing the sample (for example the blood culture flask),
- placing a predetermined amount, for example 1 mL, of a sample containing microorganisms, for example a positive blood culture, in the sample well 4 of the extraction system 2,
- loading the rack 16 equipped with the support bar 3 in an automatic machine,
- grasping the pipetting element 10 mounted on the support bar 3 by the manipulating part 18,
- withdrawing a predetermined amount, for example 500 µL, of the selective lysis buffer L contained in the reagent well 5 by the pipetting element 10,
- placing the withdrawn selective lysis buffer in the sample well 4, by the pipetting element 10,
- mixing the sample and the selective lysis buffer contained in the sample well 4 by the pipetting element 10,
- repositioning the pipetting element 10 on the support bar 3,
- incubating the mixture for a predetermined time, for example between 1 and 5 minutes, preferably for 2 minutes, at room temperature so as to lyse cells and/or particles that are not micro-organic contained in the sample and/or to lyse predetermined microorganisms contained in the sample in order to supply a lysed sample, also called lysate,
- grasping the filtering and transfer device 11 mounted on the support bar 3 by the manipulating part 18,
- applying and maintaining a partial vacuum between −50 mbar and −980 mbar relative to atmospheric pressure, preferably at about −600 mbar relative to atmospheric pressure, in the hollow body 12 of the filtering and transfer device 11,
- at least partially immersing the distal end portion 12.2 of the filtering and transfer device 11 in the lysed sample contained in the sample well 4,
- filtering with aspiration, for example for 2 minutes, at least part of the lysed sample through the filtering element 13,
- capturing and accumulating microorganisms in the filtering element 13,
- immersing under aspiration, at least partially, the distal end portion 12.2 of the filtering and transfer device 11 in the washing reagent contained in the washing well 6.1,
- washing the filtering element 13 and the captured and accumulated microorganisms under aspiration, in the washing reagent contained in the washing well 6.1,
- immersing under aspiration, at least partially, the distal end portion 12.2 of the filtering and transfer device 11 in the washing reagent contained in the washing well 6.2,
- washing the filtering element 13 and the captured and accumulated microorganisms under aspiration, in the washing reagent contained in the washing well 6.2,
- returning the hollow body 12 of the filtering and transfer device 11 to atmospheric pressure or slight overpressure,
- resuspending the microorganisms in a saline solution S1, for example at 0.45%, contained in the release well 26 for example arranged on the rack 16 near the support bar 3, the resuspending step comprising the following steps:
  - immersing, at atmospheric pressure or at slight overpressure (50 to 200 mbar), at least partially, the distal end portion 12.2 of the filtering and transfer device 11 in the saline solution S1 contained in the release well 26,
  - repeatedly contacting, for example by a reciprocating vertical movement of the release well 26 and/or of the filtering and transfer device 11, the filtering element 13 with an inner layer 26.1 of crosslinked silicone, at least partly covering the inside surface of the release well 26, for a predetermined time so as to resuspend the microorganisms accumulated by the filtering element 13 in the saline solution S1 contained in the release well 26, wherein the contacting step may for example consist of applying a vibration between 0.1 and 200 Hz, for example between 10 and 100 Hz, preferably 50 Hz, to the filtering and transfer device 11 for a predetermined time, and for example for 30 seconds,
- optionally, performing this contacting repeatedly,
- measuring the optical density (OD), calculating the dilution required and adjusting the OD by pipetting a volume of saline solution present in reserve in the washing well 6.3 as a function of the calculation carried out,
- withdrawing, from the release well 26, a predetermined amount of the saline solution S1 containing the microorganisms, preferably between 100 and 300 µL and for example 145 or 285 µL,
- introducing the withdrawn saline solution into an analysis container 27, for example arranged on the rack 16 near the release well 26, containing a predetermined amount, for example between 2 and 4 mL, preferably 3 mL, of saline solution S2, for example at 0.45%,
- transferring the consumable contained in the analysis container 27, into an antibiogram analyzer,
- performing an antibiogram analysis on the consumable that has been transferred.

According to one embodiment of the second extraction method, the latter comprises a step consisting of measuring the optical density of the saline solution S1 contained in the release well 26.

According to one embodiment of the second extraction method, the latter comprises a step consisting of adjusting to 0.5 µF the concentration of microorganisms in the saline solution S1 contained in the release well 26 by adding saline solution withdrawn from the well 6.3 containing a reserve of 0.45% saline solution.

According to one embodiment of the second extraction method, the analysis container 27 could be mounted, for example removably, directly on the support bar 3.

According to a variant embodiment of the second extraction method, the step of resuspending the microorganisms could consist of rubbing the filtering element 13 on a nylon grating wetted beforehand with a saline solution at 0.45%.

According to yet another variant embodiment of the second extraction method, the resuspending step could comprise the following steps:
- introducing, at least partially, the filtering and transfer device 11 into the release well 26,
- cutting out the filtering element 13, for example by a cutting component inserted in the release well 26,
- releasing the filtering element 13 in the saline solution S1 contained in the release well 26,
- causing movement of the release well 26 for a predetermined time, for example for 30 seconds to 1 minute, so as to release the microorganisms accumulated in the filtering element 13 and resuspend them in the saline solution S1 contained in the release well 26.

Figure 9:
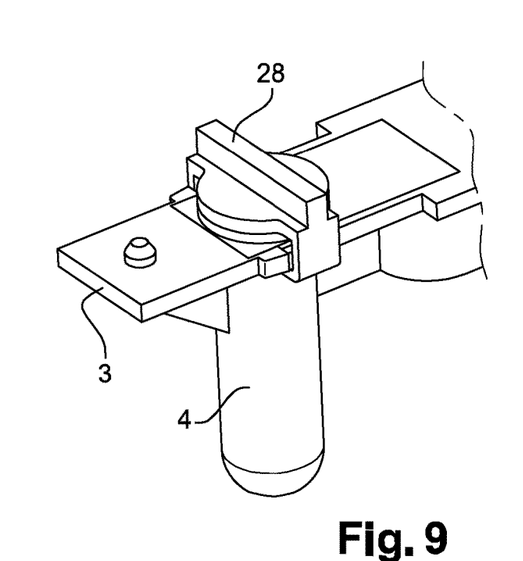
FIGS. 9 and 10 are perspective partial views of an extraction system according to a third embodiment of the invention.
Figure 10:
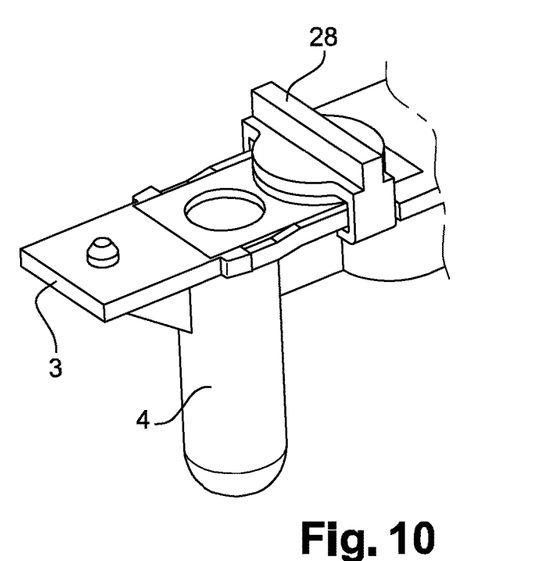

FIGS. 9 and 10 show an extraction system 2 according to a third embodiment, which differs from the first embodiment essentially in that the extraction system 2 comprises a sealing device 28 movable between a sealing position in which the sealing device 28 seals the sample well 4 and a release position in which the sealing device 28 releases the sample well 4 at least partly. The sealing device 28 may for example be mounted pivoting or sliding on the support bar 3. Furthermore, the rack 16 could be configured for automatically moving the sealing device 28 into the sealing position during positioning of the support bar on the rack 16.

The support bar 3 could additionally comprise a locking device configured for interacting with a rack 16 so as to lock the support bar 3 on the rack 16. The locking device could for example comprise (see FIG. 2) a locking element, such as a locking lug, configured for interacting with the rack so as to immobilize the support bar 3 in a Y direction of a Cartesian system, and a retaining element, such as a steel ball, configured for interacting with a permanent magnet provided on the rack 16 so as to immobilize the support bar 3 in a Z direction of the Cartesian system during insertion of the bar in the rack. The steel ball could however be replaced for example with a retaining recess configured for receiving a retaining lug provided on the rack.

It goes without saying that the invention is not limited to just the embodiment of this extraction system described above as an example, on the contrary it covers all the variant embodiments.

The invention claimed is:

1. A method for identifying and/or characterizing microorganisms contained in a sample, the method comprising:
   providing an extraction system comprising:
   - a support bar comprising a sample well, a reagent well containing a selective lysis buffer, at least one washing well containing a washing reagent, and at least one protection and retention housing,
   - a pipetting element removably mounted on the support bar and extending at least partially into the at least one protection and retention housing, and
   - a filtering and transfer device removably mounted on the support bar and extending at least partially into the at least one protection and retention housing, said filtering and transfer device comprising:
     - a hollow body having an elongated shape and comprising a proximal end portion and a distal end portion, and
     - a filtering element fixed to the distal end portion of the hollow body,
   introducing a predetermined amount of a sample containing microorganisms in the sample well,
   withdrawing a predetermined amount of the selective lysis buffer contained in the reagent well by the pipetting element,
   placing the withdrawn selective lysis buffer in the sample well by the pipetting element,
   lysing cells and/or particles that are not micro-organic contained in the sample and/or lysing predetermined microorganisms contained in the sample so as to supply a lysed sample,
   at least partially immersing the filtering and transfer device in the lysed sample contained in the sample well,
   filtering at least part of the lysed sample through the filtering element under aspiration,
   capturing and accumulating microorganisms in the filtering element,
   at least partially immersing the filtering and transfer device in the washing reagent contained in the at least one washing well,
   washing the filtering element and the captured and accumulated microorganisms in the washing reagent contained in the at least one washing well,
   transferring, by the filtering and transfer device, the washed microorganisms onto an analysis support or into a receiver, the transferring including depositing, by the filtering and transfer device, at least one part of the washed microorganisms onto one or more predetermined spots of a MALDI-TOF MS analysis plate, and
   analyzing the transferred microorganisms so as to identify and/or characterize the transferred microorganisms, the analyzing including performing a mass spectrometry analysis of the MALDI-TOF type on the microorganisms deposited on the MALDI-TOF MS plate,
   wherein the filtering element has a cylindrical shape with a diameter adapted to the diameter of a spot of the MALDI-TOF MS analysis plate, and has a flat or hemispherical distal portion that protrudes from the distal end portion of the hollow body.

2. The method according to claim 1, wherein the transferring further comprises resuspending at least part of the washed microorganisms in a saline solution contained in a release well.

3. The method according to claim 2, wherein the resuspending comprises:
   at least partially immersing the filtering and transfer device in the saline solution contained in the release well, and
   repeatedly contacting the filtering element with an inner layer of crosslinked silicone at least partly covering the inside surface of the release well for a predetermined time.

4. The method according to claim 3, further comprising:
   measuring the optical density of the saline solution contained in the release well and containing at least part of the washed microorganisms,
   adjusting the concentration of microorganisms in the saline solution contained in the release well by adding saline solution to the release well,
   withdrawing, from the release well, a predetermined amount of the saline solution containing the microorganisms, and introducing the withdrawn saline solution into an analysis container containing a predetermined amount of saline solution.

5. The method according to claim 4, wherein the analyzing comprises:
transferring a predetermined amount of a consumable contained in the analysis container and containing the transferred microorganisms, into an antibiogram analyzer, and
performing an antibiogram analysis on the consumable transferred.

6. The method according to claim 1, wherein the protection and retention housing is arranged between the sample well and the reagent well along a longitudinal direction of the support bar.

7. The method according to claim 1, wherein the microorganisms are captured and accumulated in the filtering element and other elements contained in the sample including formed elements of blood that have been lysed with the lysis buffer pass through the filtering element.

8. The method according to claim 1, wherein the distal end portion of the hollow body and the filtering element extend into the at least one protection and retention housing.

9. The method according to claim 1, wherein the filtering and transfer device comprises an absorbent material arranged in the hollow body.

10. The method according to claim 1, wherein the support bar further comprises a release well.

11. The method according to claim 1, wherein the reagent well and the at least one washing well are each sealed by a sealing element.

12. The method according to claim 1, wherein the extraction system further comprises a sealing device movable between a sealing position in which the sealing device seals the sample well and a release position in which the sealing device releases the sample well at least partly.

13. The method according to claim 1, wherein the filtering element has a pore size in a range of from 0.1 and 10 μm.

14. The method according to claim 1, wherein the filtering element has a pore size in a range of from 0.1 to 0.8 μm.

15. The method according to claim 1, wherein the filtering element has a pore size in a range of from 0.1 to 0.45 μm.

16. The method according to claim 1, wherein the filtering element comprises a material selected from the group consisting of polyether sulfone, glass fibers, cellulose acetate, and regenerated cellulose.

17. The method according to claim 1, wherein the distal portion of the filtering element has a hemispherical shape.

* * * * *